United States Patent Office

Plant Pat. 1,378
Patented Apr. 19, 1955

1,378

ROSE PLANT

Ralph S. Moore, Visalia, Calif.

Application February 26, 1954, Serial No. 412,974

1 Claim. (Cl. 47—61)

Figure 2:
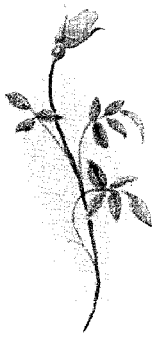

The present invention is directed to a new and distinct variety of miniature rose plant; the variety having been originated as a seedling in my nursery at Visalia, California, from the Oakington Ruby (unpatented miniature) as the seed parent, and an unknown pollen parent.

Subsequent to origination of the instant variety, it has been successfully asexually reproduced by me in my nursery, as above, by cuttings and the reproductions have been found to carry forward each and every one of the distinctive characteristics of the initial plant, and which are as follows:

The present variety of miniature rose plant is especially characterized by flowers which are more double, and are pink instead of the red shade of the seed parent, Oakington Ruby; the buds being well shaped and deep pink. The variety is well adapted for growing outdoors or in a greenhouse, for garden decoration, or as a pot plant.

Additional distinctive characteristics of the present variety of miniature rose plant are the bright clean appearance of the foliage and flowers, the variety being practically evergreen; a sweet violet fragrance; and ease of propagation, with good rapid growth.

Another distinctive characteristic of the present variety of miniature rose plant is that it bears flowers having excellent keeping quality; the petals of the older flowers falling clean before any appreciable fading, giving the plant a clean appearance at all times.

Still another characteristic of the present variety of miniature rose plant is that it is seedless.

Figure 1:
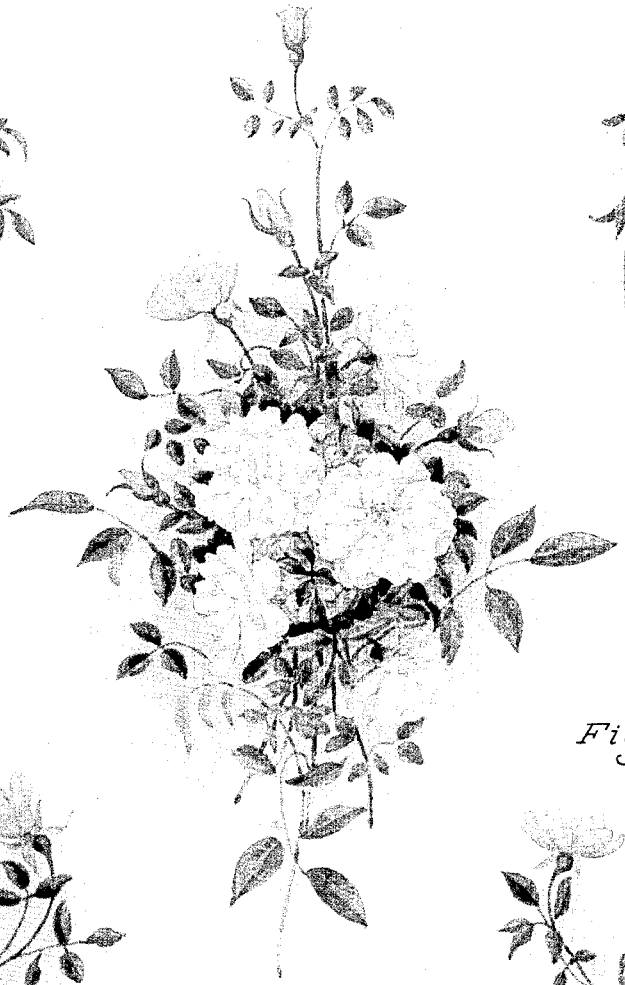
Figure 3:
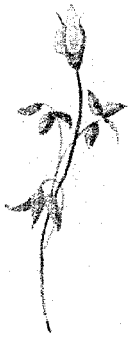
Figure 4:
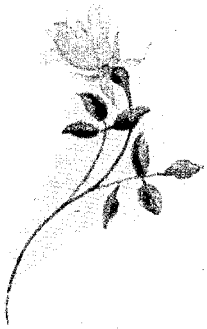
Figure 5:
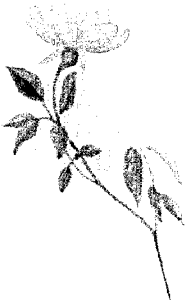

In the drawings:

Fig. 1 is an elevational view showing the flowers and buds of the variety, together with leaves and stems.

Figs. 2–5 inclusive are views showing the progressive opening of a bud to substantially a full flower.

Referring now specifically to the new and distinct variety of rose plant, the following is a detailed description thereof in outline; all major color plate identifications being by Maerz and Paul Dictionary of Color.

Type: Dwarf; bush; hardy; outdoor; greenhouse; garden decoration; pot plant.
Class: Miniature.
Flowers:
- *Continuity.*—Continuous.
- *Fragrance.*—Moderate; violet.

Flowers borne: Singly, or two to three to a stem.
Quality of bloom: Free, both outdoors and in greenhouse.
Bud:
- *Peduncle.*—Medium length; slender; stiff; almost smooth; brown hairs; reddish (7–E–6).
- *Before calyx breaks.*—Size—small. Form—pointed, without foliaceous appendages. Color—green.
- *As calyx breaks.*—Color—reddish.
- *As first petal opens.*—Size—small. Form—pointed. Color—dark pink or rose (1–A–6 shading to I–J–6). Opening: Opens well at all times.

Bloom:
- *Size, when fully open.*—Small, averaging 1″ to 1⅛″ in diameter.
- *Petalage.*—Double to very double, with from twenty-five to thirty-five or more petals arranged regularly.
- *Form.*—At first full cupped; becoming cupped; becoming later flat cupped, with outer petals rolled outward.

Petals: Thick. Satiny both sides.
- *Shape.*—Outside—obovate. Intermediate—oblanceolate. Inside—lanceolate.
- *Color.*—Top side—bright rich pink (shading from 1–E–2 to I–A–5), becoming lighter pink (1–C–1) when several days open. Under side—darker pink (1–H–5).
- *Behavior.*—Drop off cleanly without prior fading, other than shading to lighter pink, as above.
- *Flower longevity.*—Bush in garden—four to five days or longer. Cut roses indoors—three to five days.

Reproductive organs:
- *Stamens.*—Very few to none in full double flowers, although at times in early summer flowers may be semi-double and show stamens.
- *Filaments.*—Short, or semi-double flowers as above. Few to many; most with anthers. Color—white.
- *Anthers.*—Small; all open at once. Color—yellow.
- *Pollen.*—Moderate, but with more on full double flowers. Color—yellow.
- *Pistils.*—Few.
- *Styles.*—Uneven; very short; bunched.
- *Stigma.*—Greenish yellow.
- *Hips.*—None.
- *Sepals.*—Long; straight; spear shaped; recurved. Color—green, sometimes with reddish tint.
- *Seeds.*—None.

PLANT

Foliage:
- *Leaves.*—Normal, compound of five to seven leaflets. Glossy; small.
- *Leaflets.*—Ovate with acute tip; base round; margin serrate.
- *Color.*—Upper surface—green (22–L–9 shading to 21–L–7). Under surface—Lighter green (20–I–4). On leaflets the upper surface may have a reddish tinge.
- *Rachis.* — Medium size. Upper side — smooth grooved. Under side—sparsely thorny.
- *Stipules.*—Short. Narrow, with short points turning out at an angle of more than 45°.

Growth:
- *Habit.*—Dwarf; bushy. Much branched, the plant averaging about 12″ in height.
- *Growth.*—Vigorous.
- *Canes.*—Medium heavy.
- *Main stems.*—Green.
  - Thorns: Few to several. Medium length. Hooked downward, with narrow base.
  - Prickles: None.
  - Hairs: None.
- *Branches.*—Green.
  - Thorns: Few; short; hooked downward, with narrow base.
  - Prickles: None.
  - Hairs: None.
- *New shoots.*—Bronze.
  - Thorns: Very few.
  - Prickles: None.
  - Hairs: None.

The miniature rose plant, as above, being easy to propagate and a vigorous fast grower, provides an excellent variety for commercial production by nurserymen; the soft pink color of the normally double flowers, and the deep pink buds, being very attractive, and readily distinguishable from the red flowers of the seed parent, Oakington Ruby.

The miniature rose plant and its flowers, as hereinbefore described, may vary in slight detail due to climatic and soil conditions under which the variety may be grown.

Having thus described my invention I claim:

A new and distinct variety of hybrid miniature rose plant, substantially as described and illustrated, characterized—in comparison with the seed parent Oakington Ruby—by flowers more double than those of said seed parent and of a soft pink shade with deep pink buds; the flowers having a violet fragrance, keeping well on the plant, and the petals of older flowers falling clean before any appreciable fading, the foliage and the flowers having a bright clean appearance, and the plant being seedless, evergreen, easy to propagate, vigorous, and a fast grower, averaging 12″ in height under normal growing condition.

No references cited.

April 19, 1955 R. S. MOORE Plant Pat. 1,378

ROSE PLANT

WITNESS

Addison E. Avery

INVENTOR

Ralph S. Moore

Webster & Webster

ATTYS